United States Patent
Ishizaki

(10) Patent No.: US 11,559,881 B2
(45) Date of Patent: Jan. 24, 2023

(54) ARTIFICIAL EPIDERMIS STRUCTURE

(71) Applicant: Honda Motor Co., Ltd., Tokyo (JP)

(72) Inventor: Ryusuke Ishizaki, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 401 days.

(21) Appl. No.: 16/784,254

(22) Filed: Feb. 7, 2020

(65) Prior Publication Data

US 2020/0269415 A1 Aug. 27, 2020

(30) Foreign Application Priority Data

Feb. 22, 2019 (JP) .............................. JP2019-030436

(51) Int. Cl.
*B25J 9/00* (2006.01)
*A61L 27/60* (2006.01)
*B32B 5/02* (2006.01)

(52) U.S. Cl.
CPC ............. *B25J 9/0012* (2013.01); *A61L 27/60* (2013.01); *B25J 9/0006* (2013.01); *B32B 5/02* (2013.01); *B32B 2307/746* (2013.01)

(58) Field of Classification Search
CPC ................................ B25J 9/0012; A61L 27/60
See application file for complete search history.

(56) References Cited

U.S. PATENT DOCUMENTS

| | | | |
|---|---|---|---|
| 2009/0158864 A1 | 6/2009 | Hayakawa et al. | |
| 2014/0369802 A1 | 12/2014 | Sitti et al. | |

FOREIGN PATENT DOCUMENTS

| | | | |
|---|---|---|---|
| CN | 105738012 | | 7/2016 |
| JP | H0543078 | | 2/1993 |
| JP | H0599391 | | 4/1993 |
| JP | 2004230041 | | 8/2004 |
| JP | 2004230041 A | * | 8/2004 |
| JP | 2004230532 A | * | 8/2004 |
| JP | 2004337307 A | * | 12/2004 |
| JP | 2006326802 | | 12/2006 |
| JP | 2007301168 A | * | 11/2007 |

(Continued)

OTHER PUBLICATIONS

"Office Action of Japan Counterpart Application", dated Sep. 29, 2020, with English translation thereof, p. 1-p. 8.

(Continued)

*Primary Examiner* — Dale Moyer
(74) *Attorney, Agent, or Firm* — JCIPRNET

(57) ABSTRACT

Provided is an artificial epidermis structure. Three different contact states can be realized between the artificial epidermis structure and a target object. The "first contact state" is a state in which only the surface of a distal end portion of each protrusion contacts the target object. The "second contact state" is a state in which each protrusion tilts with respect to a base body corresponding to the force received from the target object and thereby the surface of a base portion and the surface of the distal end portion of each protrusion contact the target object. The "third contact state" is a state in which each protrusion further tilts with respect to the base body corresponding to an increase in the force and thereby the surface of the base body and respective surface of the distal end portion and the base portion of each protrusion contact the target object.

2 Claims, 2 Drawing Sheets

(56) References Cited

FOREIGN PATENT DOCUMENTS

| JP | 2014066526 | 4/2014 |
| JP | 2015502667 | 1/2015 |
| JP | 2018130772 | 8/2018 |

OTHER PUBLICATIONS

"Office Action of China Counterpart Application" with English translation thereof, dated Oct. 10, 2022, p. 1-p. 13.

* cited by examiner

ARTIFICIAL EPIDERMIS STRUCTURE

CROSS-REFERENCE TO RELATED APPLICATION

This application claims the priority benefit of Japan Application No. 2019-030436, filed on Feb. 22, 2019. The entirety of the above-mentioned patent application is hereby incorporated by reference herein and made a part of this specification.

BACKGROUND OF THE DISCLOSURE

Technical Field

The disclosure relates to an artificial epidermis structure used as an epidermis of a robot hand or the like.

Related Art

An artificial epidermis structure (artificial skin) is proposed which has a frictional property close to the frictional property of human skin and in which a weak frictional force can be applied to a target object when pressure received from the target object is small while a strong frictional force can be applied to the target object when the pressure is large (for example, see patent literature 1)

Specifically, the artificial skin has a concave-convex structure, and the target object first comes into contact with a convex portion formed on the surface of an epidermal membrane. Then, when the magnitude of the contact pressure of the target object increases and the convex portion sinks, the contact target object also comes into contact with a concave portion (the surface of a pseudo skin membrane). In other words, the target object is in contact with only the convex portion when the pressure of the target object with respect to the artificial skin is small; on the other hand, the target object is in contact with both the convex portion and the concave portion when the pressure of the target object with respect to the artificial skin is large. Since the friction coefficient of the convex portion is smaller than the friction coefficient of the concave portion, when the pressure of the target object with respect to the artificial skin is small, friction is generated at a lower friction coefficient compared with the case in which the pressure is large.

However, in a stage before the convex part sinks, a contact area between the convex portion and the target object is nearly unchanged; in a stage after the convex portion sinks, a contact area between the convex portion, the concave portion, and the target object is nearly unchanged. Therefore, a range of variation forms of a frictional force acting on the target object from the artificial skin is limited.

LITERATURE OF RELATED ART

Patent Literature

[Patent literature 1] Japanese Patent Laid-open No. 2004-230041

SUMMARY

The disclosure provides an artificial epidermis structure in which range expansion of variation forms of a frictional force acting on a target object can be achieved.

The artificial epidermis structure of the disclosure includes a base body, and a plurality of protrusions that protrudes from the surface of the base body; respective surface of a distal end portion and a base portion of the protrusion is different in friction coefficient, and the protrusion is flexible or is capable of tilting with respect to the base body.

According to the artificial epidermis structure having this configuration, three different contact states, that is, first-third contact states can be realized between the artificial epidermis structure and a target object corresponding to the strength of a force received from the target object. The "first contact state" is a state in which only the surface of the distal end portion of each of the plurality of protrusions is in contact with the target object. The "second contact state" is a state in which each of the plurality of protrusions bends or tilts with respect to the base body corresponding to the force (force including force components in a direction perpendicular to the protrusion direction of the protrusions from the surface of the base body) received from the target object and thereby the surface of the base portion and the surface of the distal end portion of each of the plurality of protrusions are in contact with the target object. The "third contact state" is a state in which each of the plurality of protrusions further bends or tilts with respect to the base body corresponding to an increase in the force and thereby the surface of the base body and respective surface of the distal end portion and the base portion of each of the plurality of protrusions are in contact with the target object.

Along with the increase in the force of the artificial skin structure received from the target object, the contact state transitions in the order of the first contact state, the second contact state, and the third contact state, and thereby a contact area between the artificial skin structure and the target object increases gradually. On the contrary, along with a decrease in the force of the artificial skin structure received from the target object, the contact state transitions in the order of the third contact state, the second contact state, and the first contact state, and thereby the contact area of the artificial skin structure and the target object decreases gradually.

In addition, since the friction coefficients of the surface of the distal end portion and the surface of the base portion of the protrusion are different, during the transition between the first contact state and the second contact state, the frictional force acting between the artificial skin structure and the target object can be changed in an form different from a case in which the frictional force is changed only by the change in the contact area between the artificial skin structure and the target object. Accordingly, from the artificial skin structure, range expansion of variation forms of the frictional force acting on the target object can be achieved.

In the artificial epidermis structure of the disclosure, preferably, the friction coefficient of respective surface of the distal end portion and the base portion of the protrusion is different from the friction coefficient of the surface of the base body.

According to the artificial epidermis structure having this configuration, since the friction coefficients of the surface of the distal end portion and the surface of the base portion of the protrusion are different from the friction coefficient of the surface of the base body, during the transition between the second contact state and the third contact state, the frictional force acting between the artificial skin structure and the target object can be changed in the form different from the case in which the frictional force is changed only by the change in the contact area between the artificial skin structure and the target object.

In the artificial epidermis structure of the disclosure, preferably, the friction coefficient of the surface of the distal end portion of the protrusion is smaller than the friction coefficient of the surface of the base portion of the protrusion.

According to the artificial epidermis structure having this configuration, in the second contact state, compared with the first contact state, the contact area between the artificial skin structure (or each protrusion) and the target object increases, and an average friction coefficient of the artificial skin structure at the contact point increases. Therefore, during the transition between the first contact state and the second contact state, the frictional force acting between the artificial skin structure and the target object can be changed larger than the case in which the friction force is changed only by the change in the contact area between the artificial skin structure and the target object.

In the artificial epidermis structure of the disclosure, preferably, the friction coefficient of the surface of the distal end portion of the protrusion is smaller than the friction coefficient of the surface of the base portion of the protrusion, and the friction coefficient of the surface of the base portion of the protrusion is smaller than the friction coefficient of the surface of the base body.

According to the artificial epidermis structure having this configuration, in the second contact state, compared with the first contact state, the contact area between the artificial skin structure (or each protrusion) and the target object increases, and the average friction coefficient of the artificial skin structure at the contact point increases. Therefore, during the transition between the first contact state and the second contact state, the frictional force acting between the artificial skin structure and the target object can be changed larger than the case in which the frictional force is changed only by the change in the contact area between the artificial skin structure and the target object. In the third contact state, compared with the second contact state, the contact area between the artificial skin structure and the target object increases, and the average friction coefficient of the artificial skin structure at the contact point increases. Therefore, during the transition between the second contact state and the third contact state, the frictional force acting between the artificial skin structure and the target object can be changed larger than the case in which the friction force is changed only by the change in the contact area between the artificial skin structure and the target object.

In the artificial epidermis structure of the disclosure, preferably, at least some protrusions of the plurality of protrusions are configured to be capable of at least partially sinking with respect to the base body so that the protrusion amount of the at least some protrusions from the surface of the base body is reduced.

According to the artificial epidermis structure having this configuration, a fourth contact state that is different from any one of the three contact states can be realized between the artificial epidermis structure and the target object. The "fourth contact state" is a state in which each of the plurality of protrusions sinks with respect to the base body corresponding to the force (force including force components in a direction opposite to the protrusion direction of the protrusions from the surface of the base body) received from the target object and thereby the surface of the base body and the surface of respective distal end portion of the plurality of protrusions are in contact with the target object. Accordingly, from the artificial skin structure, range expansion of variation forms of the frictional force acting on the target object can be achieved.

DESCRIPTION OF THE EMBODIMENTS

First Embodiment (Configuration)

Figure 1:
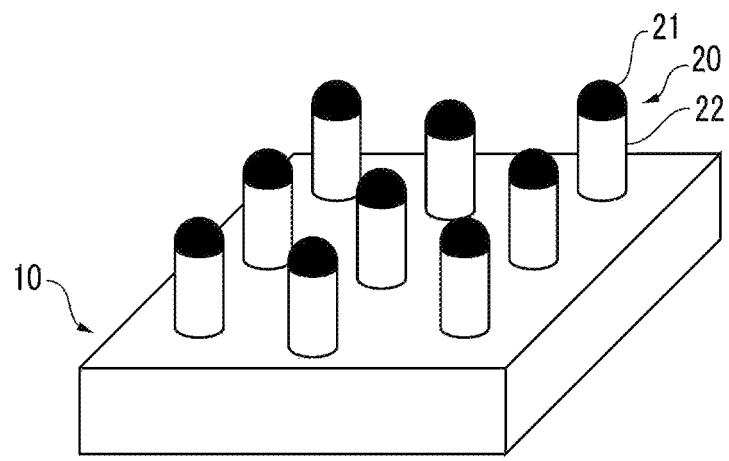
FIG. 1 is a schematic illustration diagram of a configuration of an artificial epidermis structure used as a first embodiment of the disclosure.

An artificial epidermis structure used as a first embodiment of the disclosure shown in FIG. 1 includes a base body 10 and a plurality of protrusions 20 protruding from the surface of the base body 10. The protrusion 20 includes a distal end portion 21 (upper portion) and a base portion 22 (lower portion). FIG. 1 is a schematic diagram, and respective aspect ratio of the base body 10 and the protrusion 20, a ratio of the arrangement interval of the plurality of protrusions 20 with respect to the size of the protrusion 20, a size ratio of the distal end portion 21 and the base portion 22 of the protrusion 20 and the like are different from an actual artificial epidermis structure (the same also applies to FIG. 2 and the like).

The surface of the base body 10 may have a curved shape in addition to a substantially plane shape. The direction in which the protrusion 20 protrudes from the surface of the base body 10 may be parallel or inclined with respect to a normal direction of the surface in a base end portion (lower end portion) of the protrusion 20. The distal end portion 21 is formed into a substantially semi-spherical shape for example. In addition to the substantially semi-spherical shape, the distal end portion 21 may be designed into various shapes such as a spindle shape like a conical shape or a pyramidal shape, a columnar shape like a cylindrical shape or a prismatic shape, or a frustum shape like a frusto-conical shape or a truncated pyramidal shape, and the like. The base portion 22 is formed into a substantially cylindrical shape for example. In addition to the cylindrical shape, the base portion 22 may be designed into various shapes such as other columnar shapes like an elliptical columnar shape or a prismatic shape, a frustum shape such as a frusto-conical shape or a truncated pyramidal shape, and the like.

The plurality of protrusions 20 is regularly disposed at the positions of lattice points of a triangular lattice, a square lattice or the like on the surface of the base body 10. The lattice point interval is designed in view of a desired frictional property. The plurality of protrusions 20 may be disposed to radiate from a reference point on the surface of the base body 10, or may be disposed irregularly.

The protrusion 20 is flexible or is capable of tilting with respect to the base body 10. In order to realize the flexibility or the tilting possibility of the protrusion 20, the distal end portion 21 and the base portion 22 of the protrusion 20 or the base portion 22 are/is configured by a material having flexibility at room temperature. For example, the protrusion 20 or at least the base portion 22 is configured by a flexible material such as urethane, fluoro rubber, silicone rubber, ethylene rubber, butyl rubber or the like. At least an outer-layer part of the base body 10 may be configured by the same flexible material as the base portion 20, or may be configured by a different flexible material.

Furthermore, a friction coefficient $\mu_0$ (dynamic friction coefficient) of the base body 10, a friction coefficient $\mu_1$ of the surface of the distal end portion 21 of the protrusion 20, and a friction coefficient $\mu_2$ of the surface of the base portion 22 of the protrusion 20 satisfy a condition expressed by relational expression (10).

$$\mu_1 < \mu_2 < \mu_0 \tag{10}$$

The relationship of the friction coefficients is realized by differentiating at least one of the material and the surface quality of the base body 10, and the distal end portion 21 and the base portion 22 constituting the protrusion 20.

For example, the distal end portion 21 of the protrusion 20 may be configured by a material such as a synthetic resin or the like, and the base body 10 and the base portion 22 of the protrusion 20 may be integrally configured by a material such as a silicone rubber or the like, and thereby the friction coefficient of the surface of the distal end portion 21 of the protrusion 20 and the friction coefficient of respective surface of the base body 10 and the base portion 22 of the protrusion 20 are differentiated.

The base body 10 and the protrusion 20 may be integrally configured by a material such as a silicone rubber or the like and coating may be performed on only the distal end portion 21 of the protrusion 20, and thereby the friction coefficient of the surface of the distal end portion 21 and the friction coefficient of respective surface of the base body 10 and the base portion 22 are differentiated. One type of coating may be performed on the distal end portion 21 of the protrusion 20 and another type of coating may be performed on the base portion 22 of the protrusion 20 and/or the base body 10, and thereby the friction coefficient of the surface of the distal end portion 21 and the friction coefficient of the surface of the base portion 22 and/or the friction coefficient of the surface of the base body 10 are differentiated. The base portion 22 and/or the base body 10 may be subjected to surface reforming using a dry treatment such as plasma discharge, UV irradiation and corona discharge and the like, and thereby the friction coefficient of the surface of the distal end portion 21 is differentiated from the friction coefficient of the surface of the base portion 22 and/or the friction coefficient of the surface of the base body 10.

Respective surface quality of the base body 10, the distal end portion 21, and the base portion 22 may be differentiated so that a condition expressed by relational expression (21) or (22) is satisfied among skewness $Rsk_0$ of the surface of the base body 10, skewness $Rsk_1$ of the surface of the distal end portion 21, and skewness $Rsk_2$ of the surface of the base portion 22.

$$Rsk_1 < 0 < Rsk_2 < Rsk_0 \tag{21}$$

$$Rsk_1 < Rsk_2 < 0 < Rsk_0 \tag{22}$$

Respective surface quality of the base body 10, the distal end portion 21, and the base portion 22 may be differentiated so that a condition expressed by relational expression (24) is satisfied among a surface roughness $Ra_0$ of the base body 10, a surface roughness $Ra_1$ of the distal end portion 21, and a surface roughness $Ra_2$ of the base portion 22, instead of or in addition to the skewness.

$$Ra_1 < Ra_2 < Ra_0 \tag{24}$$

(Effect)

According to the artificial epidermis structure having the above configuration, three different contact states, that is, first-third contact states can be realized between the artificial epidermis structure and a target object X corresponding to the strength of a force received from the target object X.

Figure 2A:
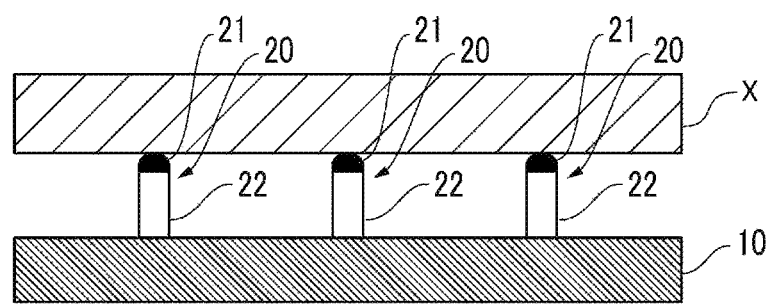
FIG. 2A is an illustration diagram related to a first contact state between the artificial epidermis structure and a target object.
Figure 2B:
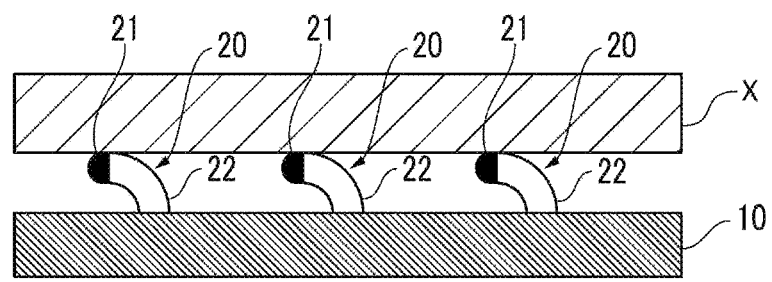
FIG. 2B is an illustration diagram related to a second contact state between the artificial epidermis structure and the target object.
Figure 2C:
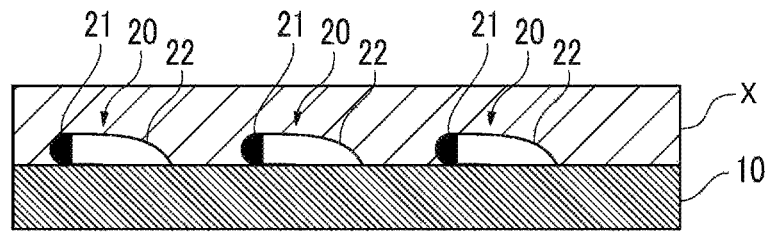
FIG. 2C is an illustration diagram related to a third contact state between the artificial epidermis structure and the target object.

As shown in FIG. 2A, the "first contact state" is a state in which only the surface of each distal end portion 21 of the plurality of protrusions 20 is in contact with the target object X. As shown in FIG. 2B, the "second contact state" is a state in which each of the plurality of protrusions 20 bends or tilts with respect to the base body 10 corresponding to the force (force including force components in a direction perpendicular to the protrusion direction of the protrusions 20 from the surface of the base body 10) received from the target object X and thereby the surface of the base portion 22 and the surface of the distal end portion 21 of each of the plurality of protrusions 20 are in contact with the target object X. As shown in FIG. 2C, the "third contact state" is a state in which each of the plurality of protrusions 20 further bends or tilts with respect to the base body 10 corresponding to an increase in the force and thereby the surface of the base body 10 and respective surface of the distal end portion 21 and the base portion 22 of each of the plurality of protrusions 20 are in contact with the target object X.

Along with the increase in the force of the artificial skin structure received from the target object X, the contact state transitions in the order of the first contact state, the second contact state, and the third contact state, and thereby a contact area between the artificial skin structure and the target object increases gradually. On the contrary, along with a decrease in the force of the artificial skin structure received from the target object X, the contact state transitions in the order of the third contact state, the second contact state, and the first contact state, and thereby the contact area between the artificial skin structure and the target object decreases gradually.

Since the friction coefficient $\mu_1$ of the surface of the distal end portion 21 of the protrusion 20 is smaller than the friction coefficient $\mu_2$ of the surface of the base portion 22 of the protrusion 20 (see relational expression (10)), in the second contact state, compared with the first contact state, the contact area between the artificial skin structure (or each protrusion 20) and the target object X increases, and an average friction coefficient of the artificial skin structure at the contact point increases. Therefore, during the transition between the first contact state (see FIG. 2A) and the second contact state (see FIG. 2C), the frictional force acting between the artificial skin structure and the target object X can be changed larger than the case in which the frictional force is changed only by the change in the contact area between the artificial skin structure and the target object X.

Furthermore, since the friction coefficient $\mu_2$ of the surface of the base portion 22 of the protrusion 20 is smaller than the friction coefficient $\mu_0$ of the base body 10 (see relational expression (10)), in the third contact state, compared with the second contact state, the contact area between the artificial skin structure and the target object X increases, and the average friction coefficient of the artificial skin structure at the contact point increases. Therefore, during the transition between the second contact state (see FIG. 2B) and the third contact state (see FIG. 2C), the frictional force acting between the artificial skin structure and the target object X can be changed larger than the case in which the frictional force is changed only by the change in the contact area between the artificial skin structure and the target object X.

Second Embodiment (Configuration)

Figure 3:
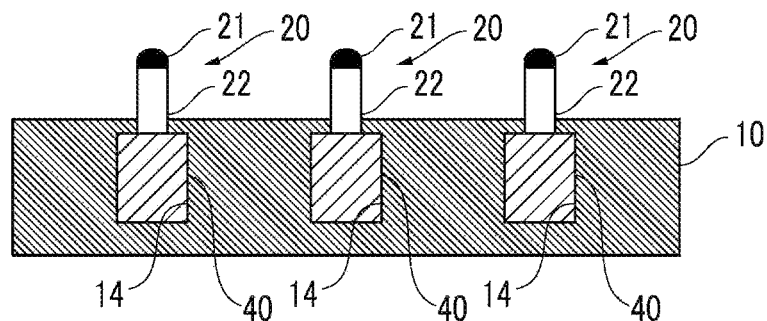
FIG. 3 is a schematic illustration diagram of a configuration of an artificial epidermis structure used as a second embodiment of the disclosure.

In an artificial epidermis structure used as a second embodiment of the disclosure shown in FIG. 3, at least some protrusions 20 of the plurality of protrusions 20 are configured to be capable of at least partially sinking with respect to the base body 10 so that the protrusion amount of the at least some protrusions 20 from the surface of the base body 10 is reduced. Specifically, an internal space 14 used as a half-open space having an opening portion on the surface of the base body 10 is formed in an outer-layer portion of the base body 10. An elastic member 40 is accommodated in the internal space 14, and a base end portion of the protrusion 20 is joined to the elastic member 40 through the opening portion of the internal space 14. The elastic member 40 is configured, for example, by an elastic material such as a porous sponge, a silicone rubber or the like.

The other configurations of the artificial epidermis structure of the second embodiment are substantially the same as the artificial epidermis structure of the first embodiment, and thus the same configurations are denoted by identical reference signs and a description thereof is omitted.

(Effect)

Figure 4:
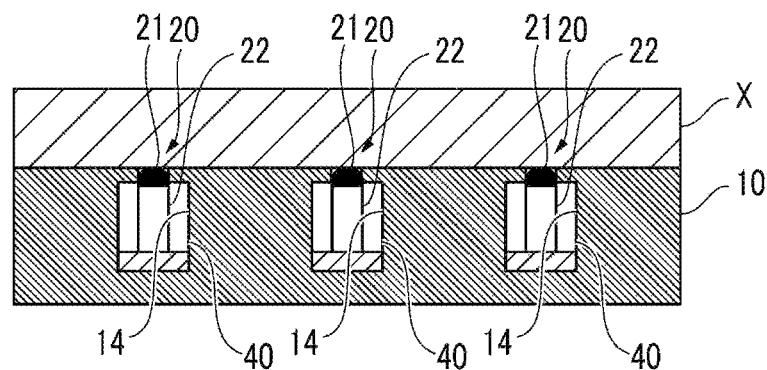
FIG. 4 is an illustration diagram related to a fourth contact state between the artificial epidermis structure and the target object.

According to the artificial epidermis structure having this configuration, a fourth contact state that is different from any one of the three contact states described above (see FIG. 2A-FIG. 2C) can be realized between the artificial epidermis structure and the target object X. As shown in FIG. 4, the "fourth contact state" is a state in which each of the plurality of protrusions 20 sinks with respect to the base body 10 corresponding to the force (force including force components in a direction opposite to the protrusion direction of the protrusions 20 from the surface of the base body 10) received from the target object X and thereby the surface of the base body 10 and the surface of each distal end portion 21 of the plurality of protrusions 20 are in contact with the target object X. Accordingly, from the artificial skin structure, range expansion of variation forms of the frictional force acting on the target object X can be achieved.

Other Embodiments of the Disclosure

In addition to relational expression (10), the friction coefficient $\mu_0$ (dynamic friction coefficient) of the base body 10, the friction coefficient $\mu_1$ of the surface of the distal end portion 21 of the protrusion 20, and the friction coefficient $\mu_2$ of the surface of the base portion 22 of the protrusion 20 may satisfy a condition expressed by a different relational expression such as any one of relational expressions (11)-(14).

$$\mu_1 < \mu_2 = \mu_0 \tag{11}$$

$$\mu_1 \leq \mu_0 < \mu_2 \tag{12}$$

$$\mu_2 < \mu_1 \leq \mu_0 \tag{13}$$

$$\mu_2 \leq \mu_0 < \mu_1 \tag{14}$$

What is claimed is:

1. An artificial epidermis structure, comprising: a base body, and a plurality of protrusions that protrudes from a surface of the base body,
    wherein respective surface of a distal end portion and a base portion of the protrusion is different in friction coefficient, and the protrusion is flexible or is capable of tilting with respect to the base body,
    wherein the friction coefficient of the surface of the distal end portion of the protrusion is smaller than the friction coefficient of the surface of the base portion of the protrusion, and the friction coefficient of the surface of the base portion of the protrusion is smaller than the friction coefficient of the surface of the base body.

2. The artificial epidermis structure according to claim 1, wherein at least some protrusions of the plurality of protrusions are configured to at least partially sink with respect to the base body so that the protrusion amount of the at least some protrusions from the surface of the base body is reduced.

* * * * *